(12) United States Patent
Miyachi et al.

(10) Patent No.: US 6,734,199 B1
(45) Date of Patent: May 11, 2004

(54) SUBSTITUTED BENZYLTHIAZOLIDINE-2, 4-DIONE DERIVATIVES

(75) Inventors: Hiroyuki Miyachi, Kazo (JP); Masahiro Nomura, Shimotsuga-gun (JP); Takahiro Tanase, Shimotsuga-gun (JP); Koji Murakami, Oyama (JP); Masaki Tsunoda, Kasukabe (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/049,904

(22) PCT Filed: Aug. 18, 2000

(86) PCT No.: PCT/JP00/05521

§ 371 (c)(1),
(2), (4) Date: Feb. 20, 2002

(87) PCT Pub. No.: WO01/14351

PCT Pub. Date: Mar. 1, 2001

(30) Foreign Application Priority Data

Aug. 23, 1999 (JP) ............................................ 11-235529
Aug. 10, 2000 (JP) ........................................ 2000-242707

(51) Int. Cl.[7] ..................... A61K 31/426; C07D 277/34

(52) U.S. Cl. ........................................ 514/369; 548/183

(58) Field of Search ........................... 548/183; 514/369

(56) References Cited

U.S. PATENT DOCUMENTS 5,061,717 A * 10/1991 Clark et al. ................. 514/342
5,753,681 A 5/1998 Fujiwara et al.

FOREIGN PATENT DOCUMENTS

| EP | 332331 | | 9/1989 |
|---|---|---|---|
| EP | 0 846 693 | * | 6/1998 |
| JP | 8-333355 | | 12/1996 |
| JP | 9-48771 | | 2/1997 |
| JP | 9-301963 | | 11/1997 |
| WO | 97/32863 | | 9/1997 |
| WO | WO 03/045945 A1 | | 6/2003 |

OTHER PUBLICATIONS

K. Murakami et al.: "A Novel Insulin Sensitizer Acts as a Coligand for Peroxisome Proliferator–Activated Receptor–α (PPAR–α) and PPAR–γ", Diabetes, 47, pp. 1841–1847, 1998.
Ide Tomohiro et al.: "Zuker fatty Rat ni okeru Kanshishitsu Taisha taisuru PPAR α Kasseika no Eikyou", Diabetes Frontier, 9(3), pp. 345–346, 1998.
M. Nomura, et al., Bioorganic & Medicinal Chemistry Letters, vol. 9, No. 4, pp. 533–538, XP–004156083, "(3–Substituted Benzyl)Thiazolidine–2,4–Diones as Structurally New Antihyperglycemic Agents", Feb. 22, 1999.
B. Hulin, et al., Journal of Medicinal Chemistry, vol. 35, pp. 1853–1864, XP–002932592, "Novel Thiazolidine–2, 4–Diones as Potent Euglycemic Agents", 1992.

* cited by examiner

*Primary Examiner*—Joseph K. McKane
*Assistant Examiner*—Rebecca Anderson
(74) *Attorney, Agent, or Firm*—Oblon, Spivak, McClelland, Maier & Neustadt, P.C.

(57) ABSTRACT

The invention provides novel substituted benzylthiazolidine-2,4-dione derivatives which increase the transactivation action of receptor as a ligand of human peroxisome proliferator-activated receptor (PPAR) and exhibit the blood glucose-decreasing action and lipid-decreasing action, and a process for preparing them.

The invention relates to substituted benzylthiazolidine-2,4-dione derivatives represented by the general formula (1)

(1)

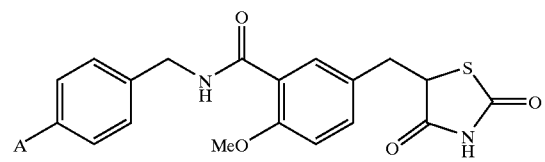

[wherein A denotes a phenyl group which is unsubstituted or may have substituents, phenoxy group which is unsubstituted or may have substituents or benzyloxy group which is unsubstituted or may have substituents], their medicinally acceptable salts, their hydrates and a process for preparing them.

9 Claims, No Drawings

SUBSTITUTED BENZYLTHIAZOLIDINE-2,4-DIONE DERIVATIVES

This application is a 371 of PCT/JP00/05521 filed Aug. 18, 2000.

TECHNICAL FIELD

The present invention relates to substituted benzylthiazolidine-2,4-dione derivatives effective for the prevention and/or therapy of metabolic diseases such as diabetes and hyperlipidemia as agonists of peroxisome proliferator-activated receptor (abbreviated as PPAR) being nuclear receptor, in particular, as agonists of human PPAR, their addition salts, process for preparing them, and medicinal compositions containing these compounds.

BACKGROUND TECHNOLOGIES

The peroxisome proliferator-activated receptor(PPAR) is a ligand-dependent transcription factor that belongs to nuclear receptor superfamily similarly to steroid receptor, retinoid receptor, thyroid receptor, etc., and three isoforms ($\alpha$ type, $\beta$ (or $\delta$) type and $\gamma$ type) with different histological distribution have been identified hitherto in human and various animal species (Proc. Natl. Acad. Sci., 1992, 89, 4653). Thereamong, the PPAR$\alpha$ is distributed in the liver, kidney, etc. with high catabolic capacity for fatty acids and, particularly high expression is recognized in the liver, (Endo-crinology, 1995, 137, 354), positively or negatively controlling the expression of genes related to the metabolism and the intracellular transport of fatty acids (e.g. acyl CoA synthetic enzyme, fatty acid-binding protein and lipoprotein lipase) and apolipoprotein (AI, AII, CIII) genes related to the metabolisms of cholesterol and triglycerides. The PPAR$\beta$ is expressed ubiquitously in the tissues of organisms including around nerve cells. At present, the physiological significance of PPAR$\beta$ is unclear. The PPAR$\gamma$ is highly expressed in the adipocytes and contributed to the differentiation of adipocytes (J. Lipid Res., 1996, 37, 907). In this way, each isoform of PPAR play specific functions in the particular organs and tissues.

Moreover, it is reported that a knock-out mouse of PPAR$\alpha$ exhibits hypertriglyceridemia with ageing and becomes obesity mainly by increasing the white adipocytes (J. Biol. Chem., 1998, 273, 29577), hence the relevance between activation of PPAR$\alpha$ and decreasing action of lipids (cholesterol and triglyceride) in blood is suggested strongly.

On the other hand, fibrates and statins are widely used so far as the therapeutic drugs for hyperlipidemia. However, the fibrate type drugs have only weak decreasing action of cholesterol, while the statin type drugs have weak decreasing action of free fatty acids and triglycerides. Moreover, with respect to the fibrate type drugs, various adverse effects such as gastrointestinal injury, anthema, headache, hepatic disorder, renal disorder and biliary calculus are reported. The reason is considered to be due to that the fibrate type drugs exhibit extensive pharmacological function.

On the other hand, it is ascertained that the major intracellular target protein of Troglitazone, Pioglitazone and Rosiglytazone being a series of thiazolidine-2,4-dione derivatives that are the therapeutic drugs for type II diabetes (noninsulindependent diabetes) and exhibit blood glucose-decreasing action, improving action on hyperinsulinemia, etc. are PPAR$\gamma$, and these drugs increase the transactivation of PPAR$\gamma$ (Endocrinology, 1996, 137, 4189, Cell., 1995, 83, 803, Cell., 1995, 83, 813). Hence, PPAR$\gamma$-activator (agonist) that increases the transactivation of PPAR$\gamma$ is important as antidiabetic drug.

As described, when considering the roles of transcription factor called PPAR on the function on adipocytes and the controlling mechanisms of glucose metabolism and lipid metabolism, if a compound that binds directly to as a ligand of PPAR, in particular, human PPAR and can activate human PPAR could be created, it would be reasonable to expect the medicinal use as a compound that exhibits blood glucose-decreasing action and/or decreasing action of lipids (both of cholesterol and triglyceride) in blood due to very specific mechanism.

For compounds having an affinity to PPAR$\alpha$ as ligands of PPAR$\alpha$, HEPE (hydroxyeicosapentaenoic acid) produced via oxidation with cytochrome P-450 and eicosanoides in HETE (hydroxyeicosatetraenoic acid) groups, in particular, 8-HETE, 8-HEPE, etc. are reported in addition to LTB$_4$, being a metabolite of arachidonic acid (Proc. Natl. Acad. Sci., 1997, 94, 312). However, these endogenous unsaturated fatty acid derivatives are unstable metabolically and chemically and cannot be offered as medicinal drugs.

Moreover, with Troglitazone, the occurrence of serious adverse effect on liver is reported rarely, hence the development of a therapeutic drug for type II diabetes with effectiveness and high safety is being sought.

Now, as compounds with similar structure to the inventive substituted benzylthiazolidine-2,4-dione derivatives, thiazolidine-2,4-dione derivatives in Japanese Unexamined Patent Publication Nos. Sho 55-22636, Sho 60-51189, Sho 61-85372, Sho 61-286376, Hei 1-131169, Hei 2-83384, Hei 5-213913, Hei 8-333355, Hei 9-48771 and Hei 9-169746, European Patent Open No. 0441605, WO-92/07839, etc. are known. However, all of these compounds are thlzolidine-2,4-dione derivatives with different structure from the inventive compounds.

With regard to patents etc. reporting the agonistic effect on PPAR $\alpha$, WO-97/25042, WO-97/36579, etc. are reported, but all of these have different structure from the inventive compounds and the transactivation function of PPAR$\alpha$ is also never satisfied in strength.

Both the hyperlipidemia and the diabetes are risk factors of arterosclerosis and, from a viewpoint of the prevention of arterosclerosis, in particular, coronary arterosclerosis, the development of a therapeutic drug for metabolic diseases with effectiveness and high safety is desired clinically.

DISCLOSURE OF THE INVENTION

As a result of diligent studies paying an attention to such specific roles on the lipid metabolism of human PPAR, differentiation of adipocytes, etc. aiming at the creation of structurally novel drug with effectiveness and high safety as a therapeutic drug for metabolic diseases, the inventors have found that novel substituted benzylthiazolidine-2,4-dione derivatives represented by the following general formula (1) have excellent transactivation function of human PPAR, and exhibit the blood glucose-decreasing action and the lipid-decreasing action, leading to the completion of the invention.

Namely, the invention relates to substituted benzylthiazolidine-2,4-dione derivatives represented by the general formula (1)

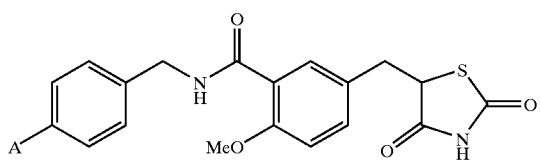

[wherein A denotes a phenyl group which is unsubstituted or may have substituents, phenoxy group which is unsubstituted or may have substituents or benzyloxy group which is unsubstituted or may have substituents], their medicinally acceptable salts and their hydrates.

The salts of the compounds represented by the general formula (1) in the invention are of common use and metal salts, for example, alkali metal salts (e.g. sodium salt, potassium salt, etc.), alkaline earth metal salts (e.g. calcium salt, magnesium salt, etc.), aluminum salt, and other pharmacologically acceptable salts are mentioned.

Moreover, the compounds represented by the general formula (1) in the invention sometimes include optical isomers based on thiazolidine-2,4-dione ring portion, but all of such isomers and their mixtures are to be included in the scope of the invention.

Furthermore, for the compounds represented by the general formula (1), the existence of various tautomers is considered. These are, for example, as shown in the following formulae.

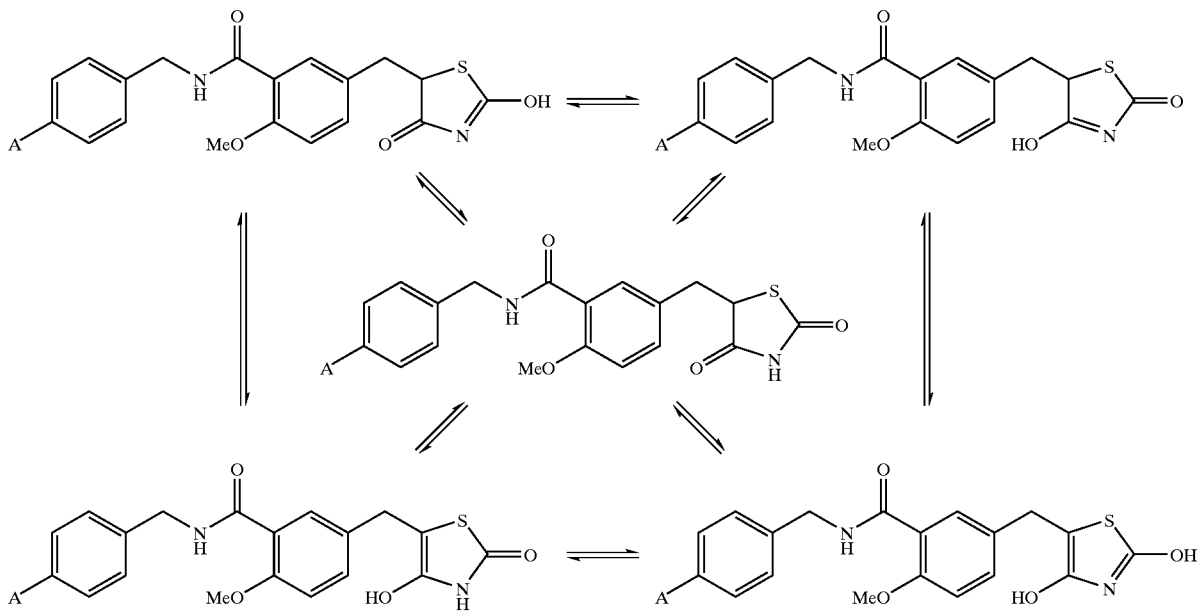

[wherein A denotes a phenyl group which is unsubstituted or may have substituents, phenoxy group which is unsubstituted or may have substituents or benzyloxy group which is unsubstituted or may have substituents]. In the general formula (1) aforementioned, all of these isomers and their mixtures are to be included in the scope of this invention.

In the general formula (1) of the invention, for the substituents permissible in "phenyl group which is unsubstituted or may have substituents, phenoxy group which is unsubstituted or may have substituents or benzyloxy group which is unsubstituted or may have substituents", lower alkyl group with carbon atoms of 1 to 4, lower alkoxy group with carbon atoms of 1 to 3 and halogen atom are mentioned.

According to the invention, the compounds being said the general formula (1) can be prepared, for example, through the following process (Scheme 1).

Scheme 1

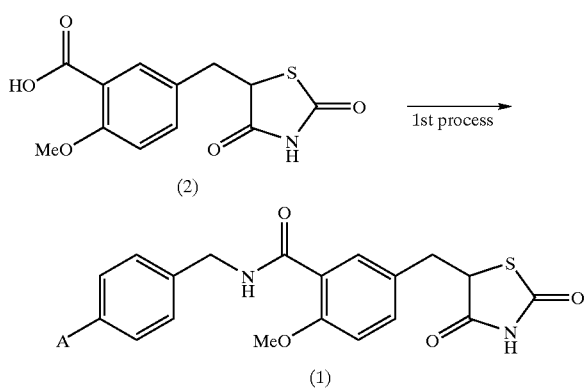

Namely, the compounds represented by the general formula (1) can be prepared by reacting (first process) publicly known (Japanese Unexamined Patent Publication No. Hei 8-333355) compound (2) and the compounds represented by the general formula (3)

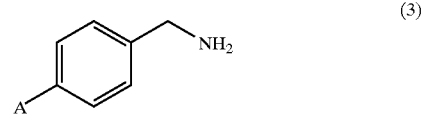

[wherein A denotes a phenyl group which is unsubstituted or may have substituents, phenoxy group which is unsubstituted or may have substituents or benzyloxy group which is unsubstituted or may have substituents].

The first process can be performed by leaving the carboxyl group as it is, or converting it to the reactive derivative.

As the "reactive derivative group of the carboxyl group", acid chloride, acid bromide, acid anhydride, carbonylimidazole or the like can be mentioned. In the case of the reaction using the reactive derivative, the reaction can be performed in a solvent such as methylene chloride, chloroform, dioxane or N,N-dimethylformamide in the presence or absence of, for example, alkali metal hydride such as sodium hydride, alkali metal hydroxide such as sodium hydroxide, alkali metal carbonate such as potassium carbonate, or organic base such as pyridine or triethylamine as a base.

In the case of conducting the reaction by leaving the carboxylic acid as it is, the reaction can be performed in a solvent such as methylene chloride, chloroform, dioxane or N,N-dimethylformamide in the presence of condensing agent in the presence or absence of base, in the presence or absence of additive.

As the condensing agent, for example, dicyclohexylcarbodiimide, 1-[3-(dimethylamino)propyl]-3-ethylcarbodiimide hydrochloride, diethyl cyanophosphate, diphenylphosphoric azide, carbonyldiimidazole or the like can be mentioned. As the base, for example, alkali metal hydroxide such as sodium hydroxide, alkali metal carbonate such as potassium carbonate, or organic base such as pyridine or triethylamine can be mentioned. As the additive, N-hydroxybenzotriazole, N-hydroxysuccinimide, 3,4-dihydro-3-hydroxy-4-oxo-1,2,3-benzotriazine or the like can be mentioned. The reaction can be performed at a reaction temperature of −20° C. to 100° C., preferably at 0° C. to 50° C.

As the administering form of the novel compounds of the invention, for example, oral administration with tablet, capsule, granule, powder, inhalant, syrup or the like, or parenteral administration with injection, suppository or the like can be mentioned.

Best Embodiment to Put the Invention Into Practice

In following, the invention will be illustrated based on concrete examples, but the invention is not confined to these examples.

EXAMPLE 1

N-[4-Benzyloxyphenyl)methyl]-5-[(2,4-Dioxothiazolidin-5-yl)-methyl]-2-methoxybenzamide 5-[(2,4-Dioxothiazolidin-5-yl)methyl]-2-methoxybenzoic acid (422 mg, 1.50 mmol), triethylamine (0.523 mL, 3.75 mmol) and methylene chloride (5 mL) were mixed and ethyl chlorocarbonate (0.158 mL, 1.50 mmol) was added under cooling with ice and stirring. After stirring for 10 minutes under cooling with ice, a solution of 4-(benzyloxy)benzylamine (319 mg, 1.50 mmol) dissolved in methylene chloride (2 mL) was added. The mixture was stirred for 2 hours at room temperature, and then allowed to stand overnight. After washed with water, the reaction mixture was dried over anhydrous sodium sulfate and concentrated. The residue was dissolved in water (40 mL), which was made acidic with 10% hydrochloric acid and stirred for 30 minutes. The precipitated crystals were collected by filtration, dried, and then recrystallized from a mixed solution of ethanol and water to obtain 549 mg (77%) of the title compound as colorless powder.

Melting point 131.0–132.5° C.; Mass analysis m/z 476 (M$^+$); Elemental analysis (%) $C_{26}H_{24}N_2O_5S$: Calcd.(%) C, 65.53; H, 5.08; N, 5.88. Found (%) C, 65.68; H, 5.08; N, 5.91.

EXAMPLES 2 and 3

Similarly to Example 1, the following compounds were obtained.

EXAMPLE 2

N-[(Biphenyl-4-yl)Methyl]-5-[(2.4-Dioxothiazolidin-5-yl)Methyl]-2-Methloybenzamide Melting point 170.5–172.0° C.; Mass analysis m/z 446 (M$^+$); Elemental analysis(%) $C_{25}H_{22}N_2O_4S$: Calcd.(%) C, 67.25; H, 4.97; N, 6.27. Found (%) C, 67.29; H, 4.99; N, 6.21.

EXAMPLE 3

N-1[(4-Phenoxyphenyl)Methyl]-5-[(2,4-Dioxothiazolidin-5-yl Meth-yl]-2-Methoxybenzamide Melting point 87.0–89.0° C.; Mass analysis m/z 462(M$^+$); Elemental analysis(%) $C_{25}H_{22}N_2O_5S \cdot 1/5H_2O$: Calcd.(%) C, 64.42; H, 4.84; N, 6.01. Found (%) 64.17; H, 4.81; N, 6.03.

EXAMPLES 4 Through 13

Similary to Example 1, the compounds in Table 1 were obtained.

TABLE 1

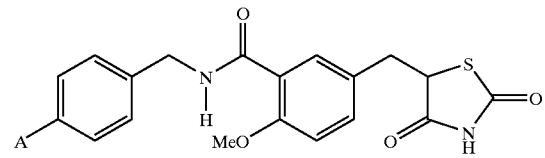

| Example | A | Melting point (° C.) | Mass analysis (m/z) | Charac. formula | Elemental analysis (%) |
|---|---|---|---|---|---|
| 4 | 4-OPh(2-OMe) | Amorphous | 492(M$^+$) | $C_{26}H_{24}N_2O_6S$ | Cald.; C63.40, H4.91, N5.69 Found; C63.05, H4.95, N5.57 |

TABLE 1-continued

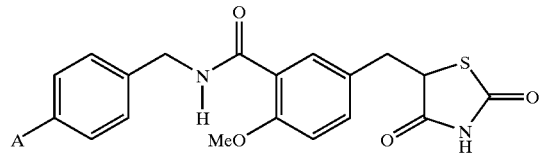

| Example | A | Melting point (° C.) | Mass analysis (m/z) | Charac. formula | Elemental analysis (%) |
|---|---|---|---|---|---|
| 5 | 4-OPh(3-OMe) | Amorphous | 492($M^+$) | $C_{26}H_{24}N_2O_6S$ | Cald.; C63.40, H4.91, N5.69 Found; C63.13, H4.95, N5.54 |
| 6 | 4-OPh(4-OMe) | Amorphous | 492($M^+$) | $C_{26}H_{24}N_2O_6S$ | Cald.; C63.40, H4.91, N5.69 Found; C63.05, H4.99, N5.54 |
| 7 | 4-OPh(3-Me) | 154.0–156.0 | 476($M^+$) | $C_{26}H_{24}N_2O_5S$ | Cald.; C65.53, H5.08, N5.88 Found; C65.29, H5.16, N5.79 |
| 8 | 4-OPh(4-Me) | 146.0–147.0 | 476($M^+$) | $C_{26}H_{24}N_2O_5S$ | Cald.; C65.53, H5.08, N5.88 Found; C65.20, H5.10, N5.87 |
| 9 | 4-Ph(4-Cl) | 200.0–202.0 | 480($M^+$) | $C_{25}H_{21}ClN_2O_4S \cdot \frac{1}{4}H_2O$ | Cald.; C61.85, H4.46, N5.77 Found; C61.92, H4.35, N5.74 |
| 10 | 4-Ph(4-OMe) | 201.0–202.0 | 476($M^+$) | $C_{26}H_{24}N_2O_5S \cdot \frac{1}{4}H_2O$ | Cald.; C64.92, H5.13, N5.82 Found; C65.02, H5.12, N5.81 |
| 11 | 4-OCH$_2$Ph(4-Cl) | 158.0–160.0 | 510($M^+$) | $C_{26}H_{23}ClN_2O_5S$ | Cald.; C61.11, H4.54, N5.48 Found; C61.22, H4.53, N5.46 |
| 12 | 4-OCH$_2$Ph(4-Me) | 181.0–183.0 | 490($M^+$) | $C_{27}H_{26}N_2O_5S \cdot \frac{1}{4}H_2O$ | Cald.; C65.50, H5.39, N5.66 Found; C65.37, H5.28, N5.57 |
| 13 | 4-Ph(4-Me) | 190.0–192.0 | 460($M^+$) | $C_{26}H_{24}N_2O_4S$ | Cald.; C67.81, H5.25, N6.08 Found; C67.56, H5.22, N6.02 |

<Biological Activity>

TEST EXAMPLE 1

Test of Transactivation on Peroxisome Proliferator-activated Receptors α and γ

To CHO cells cultured in a Ham's F-12 medium containing fatty acid free 10% fetal calf serum, receptor plasmid and its reporter plasmid (STRATAGENE Corp.) that express fused protein of DNA-binding domain being transcription factor of yeast with ligand-binding domain of human type PPARs α and γ (Biochemistry, 1993, 32, 5598), and β-galactosidase plasmid (Promega Corp.) for internal standard were cotransfected with lipofectamine in the serum-free state. Thereafter, testing compound and control compound (Troglitazone or Pioglitazone for control drug of PPAR γ, and (8S)-HETE for control drug of PPAR α) were dissolved into DMSO and adjusted with Ham's F-12 medium containing fatty acid free 10% fetal calf serum, so that the final concentration of DMSO became 0.01% to culture. After 24 hours, CAT activity and β-galactosidase activity were measured.

Results are shown in Table 2. From these results, it was shown that the inventive compounds had potent transactivation action on human peroxisome proliferator-activated receptors α and γ.

TABLE 2

| | Transactivation action | |
|---|---|---|
| Example | PPARα $EC_{50}$ (μmol/L) | PPARγ $EC_{50}$ (μmol/L) |
| 1 | 0.44 | — |
| 2 | 0.63 | 6.8 |
| 3 | 0.24 | 0.24 |
| Troglitazone | — | 1.15 |
| Pioglitazone | — | 0.72 |
| (8S)-HETE | 1.3 | — |

Utilizability in the Industry

From the results as described above, the inventive substitutes benzylthiazolidine-2,4-dione derivatives are novel compounds group with excellent human PPAR transactivation.

From the fact that these inventive compounds have agonistic activity on human PPAR, it can be said that they are effective compounds as blood glucose-decreasing drugs and therapeutic drugs for hyperlipidemia aforementioned.

What is claimed is:

1. A substituted benzylthiazolidine-2,4-dione derivative represented by a general formula (1)

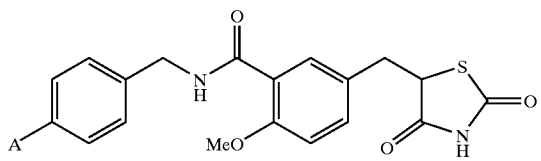

(1)

wherein A denotes a phenyl group which is unsubstituted or may have substituents, phenoxy group which is unsubstituted or may have substituents or benzyloxy group which is unsubstituted or may have substituents, their medicinally acceptable salts and their hydrates.

2. The substituted benzylthiazolidine-2,4-dione derivatives, their medicinally acceptable salts and their hydrates of claim 1, wherein A is phenyl group which is unsubstituted or may have substituents.

3. The substituted benzylthiazolidine-2,4-dione derivatives, their medicinally acceptable salts and their hydrates of claim 1, wherein A is phenoxy group which is unsubstituted or may have substituents.

4. The substituted benzylthiazolidine-2,4-dione derivatives, their medicinally acceptable salts and their hydrates of claim 1, wherein A is benzyloxy group which is unsubstituted or may have substituents.

5. A compound of claim 1, being N-[(4-benzyloxyphenyl)-methyl]-5-[(2,4-dioxothiazolidin-5-yl)methyl]-2-methoxybenzamide, its medicinally acceptable salts and its hydrates.

6. A compound of claim 1, being N-[(4-phenoxyphenyl)methyl]-5-[(2,4-dioxothiazolidin-5-yl)methyl]-2-methoxybenzamide, its medicinally acceptable salts and its hydrates.

7. A compound of claim 1, being N-[(biphenyl-4-yl)methyl]-5-[(2,4-dioxothiazolidin-5-yl)methyl]-2-methoxybenzamide, its medicinally acceptable salts and its hydrates.

8. A medicinal composition, comprising at least one substituted benzylthiazolidine2,4-dione derivative according to claim 1 and a suitable carrier.

9. A process for preparing a medicinal composition, comprising contacting at least one substituted benzylthiazolidine-2,4-dione derivative according to claim 1 with a suitable carrier.

* * * * *